(12) United States Patent
Weitz et al.

(10) Patent No.: US 10,876,156 B2
(45) Date of Patent: Dec. 29, 2020

(54) DETERMINATION OF CELLS USING AMPLIFICATION

(71) Applicant: President and Fellows of Harvard College, Cambridge, MA (US)

(72) Inventors: David A. Weitz, Bolton, MA (US); Huidan Zhang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 380 days.

(21) Appl. No.: 15/557,622

(22) PCT Filed: Mar. 11, 2016

(86) PCT No.: PCT/US2016/022021
§ 371 (c)(1),
(2) Date: Jan. 18, 2018

(87) PCT Pub. No.: WO2016/149096
PCT Pub. Date: Sep. 22, 2016

(65) Prior Publication Data
US 2018/0066305 A1 Mar. 8, 2018

Related U.S. Application Data

(60) Provisional application No. 62/133,140, filed on Mar. 13, 2015.

(51) Int. Cl.
*C12Q 1/686* (2018.01)
*C12Q 1/689* (2018.01)
(Continued)

(52) U.S. Cl.
CPC ......... *C12Q 1/686* (2013.01); *C12N 15/1075* (2013.01); *C12Q 1/6806* (2013.01);
(Continued)

(58) Field of Classification Search
None
See application file for complete search history.

(56) References Cited

U.S. PATENT DOCUMENTS

| 7,041,481 B2 | 5/2006 | Anderson et al. |
| 7,323,305 B2 | 1/2008 | Leamon et al. |

(Continued)

FOREIGN PATENT DOCUMENTS

| CN | 1477208 A | 2/2004 |
| CN | 101275164 A | 10/2008 |

(Continued)

OTHER PUBLICATIONS

Zhu et al. Highly sensitive and quantitative detection of rare pathogens through agarose droplet microfluidic emulsion PCR at the single-cell level. Lab Chip 12:3907-3913. (Year: 2012).*

(Continued)

*Primary Examiner* — Samuel C Woolwine
(74) *Attorney, Agent, or Firm* — Wolf, Greenfield & Sacks, P.C.

(57) ABSTRACT

The present invention generally relates to microfluidics and, in particular, to systems and methods for determining cells using amplification. In one set of embodiments, cells are encapsulated within droplets and nucleic acids from the cells amplified within the droplets. The droplets may then be pooled together and the amplified nucleic acids can be determined using PCR or other suitable techniques. In some embodiments, techniques such as these can be used to detect relatively rare cells that may be present, e.g., if the droplets are amplified using conditions able to selectively amplify nucleic acids arising from the relatively rare cells.

16 Claims, 3 Drawing Sheets
Specification includes a Sequence Listing.

(51) Int. Cl.
*C12N 15/10* (2006.01)
*C12Q 1/6806* (2018.01)
*C12Q 1/6886* (2018.01)

(52) U.S. Cl.
CPC .......... *C12Q 1/689* (2013.01); *C12Q 1/6886* (2013.01); *C12Q 2600/106* (2013.01); *C12Q 2600/156* (2013.01); *C12Q 2600/158* (2013.01)

(56) References Cited

U.S. PATENT DOCUMENTS

| | | |
|---|---|---|
| 7,708,949 B2 | 5/2010 | Stone et al. |
| RE41,780 E | 9/2010 | Anderson et al. |
| 7,842,457 B2 | 11/2010 | Berka et al. |
| 8,337,778 B2 | 12/2012 | Stone et al. |
| 8,765,485 B2 | 7/2014 | Link et al. |
| 9,017,948 B2 | 4/2015 | Weitz et al. |
| 9,029,085 B2 | 5/2015 | Agresti et al. |
| 9,068,210 B2 | 6/2015 | Weitz et al. |
| 9,664,619 B2 | 5/2017 | Boehm et al. |
| 9,816,121 B2 | 11/2017 | Weitz et al. |
| 9,850,526 B2 | 12/2017 | Weitz et al. |
| 10,221,437 B2 | 3/2019 | Weitz et al. |
| 10,508,294 B2 | 12/2019 | Weitz et al. |
| 10,683,524 B2 | 6/2020 | Weitz et al. |
| 2004/0180346 A1 | 9/2004 | Anderson et al. |
| 2005/0130173 A1 | 6/2005 | Leamon et al. |
| 2005/0172476 A1 | 8/2005 | Stone et al. |
| 2006/0040297 A1* | 2/2006 | Leamon ............... B01L 3/5027 435/6.18 |
| 2007/0003442 A1 | 1/2007 | Link et al. |
| 2007/0195127 A1 | 8/2007 | Anh et al. |
| 2008/0176233 A1 | 7/2008 | Nilsen et al. |
| 2008/0241841 A1 | 10/2008 | Murakawa et al. |
| 2009/0197248 A1 | 8/2009 | Griffiths et al. |
| 2010/0069250 A1 | 3/2010 | White, III et al. |
| 2010/0105112 A1 | 4/2010 | Holtz et al. |
| 2010/0124759 A1 | 5/2010 | Wang et al. |
| 2010/0136544 A1 | 6/2010 | Agresti et al. |
| 2010/0172803 A1 | 7/2010 | Stone et al. |
| 2011/0087016 A1* | 4/2011 | Suo ..................... C12Q 1/6806 536/25.41 |
| 2011/0257046 A1 | 10/2011 | Schroeder |
| 2012/0132288 A1 | 5/2012 | Weitz et al. |
| 2012/0164633 A1 | 6/2012 | Laffler |
| 2012/0164652 A1 | 6/2012 | Clemens et al. |
| 2013/0189700 A1* | 7/2013 | So ........................... G01N 1/34 435/6.12 |
| 2014/0199730 A1 | 7/2014 | Weitz et al. |
| 2014/0199731 A1 | 7/2014 | Weitz et al. |
| 2014/0227684 A1 | 8/2014 | Hindson et al. |
| 2015/0057163 A1 | 2/2015 | Rotem et al. |
| 2015/0298091 A1 | 10/2015 | Weitz et al. |
| 2015/0353999 A1 | 12/2015 | Weitz et al. |
| 2016/0265043 A1* | 9/2016 | Geng ................... C12Q 1/6858 |
| 2017/0029813 A1 | 2/2017 | Weitz et al. |
| 2017/0183701 A1 | 6/2017 | Weitz et al. |
| 2018/0016622 A1 | 1/2018 | Weitz et al. |
| 2018/0023109 A1 | 1/2018 | Weitz et al. |
| 2018/0056293 A1 | 3/2018 | Weitz et al. |
| 2018/0119212 A1 | 5/2018 | Weitz et al. |
| 2018/0171373 A1 | 6/2018 | Weitz et al. |
| 2019/0127789 A1 | 5/2019 | Weitz et al. |
| 2020/0002741 A1 | 1/2020 | Weitz et al. |
| 2020/0157593 A1 | 5/2020 | Weitz et al. |

FOREIGN PATENT DOCUMENTS

| | | |
|---|---|---|
| CN | 102260747 A | 11/2011 |
| CN | 102648053 A | 8/2012 |
| WO | WO 91/09967 A1 | 7/1991 |
| WO | WO 2004/002627 A2 | 1/2004 |
| WO | WO 2004/091763 A2 | 10/2004 |
| WO | WO 2005/021151 A1 | 3/2005 |
| WO | WO 2006/096571 A2 | 9/2006 |
| WO | WO 2008/109176 A2 | 9/2008 |
| WO | WO 2010/033200 A2 | 3/2010 |
| WO | WO 2010/080134 A1 | 7/2010 |
| WO | WO 2010/151776 A2 | 12/2010 |
| WO | WO 2011/056546 A1 | 5/2011 |
| WO | WO-2012048341 A1 * | 4/2012 ........... C12Q 1/6869 |
| WO | WO 2012/156744 A1 | 11/2012 |
| WO | WO 2013/134261 A1 | 9/2013 |
| WO | WO 2013/192351 A1 | 12/2013 |
| WO | WO 2014/145555 A1 | 9/2014 |
| WO | WO 2014/153651 A1 | 10/2014 |
| WO | WO 2014/194131 A2 | 12/2014 |
| WO | WO 2015/160919 A1 | 10/2015 |
| WO | WO 2015/161177 A1 | 10/2015 |
| WO | WO 2015/161223 A1 | 10/2015 |
| WO | WO 2015/164212 A1 | 10/2015 |
| WO | WO 2016/118870 A1 | 7/2016 |
| WO | WO 2016/149096 A1 | 9/2016 |
| WO | WO 2017/184707 A1 | 10/2017 |

OTHER PUBLICATIONS

Zeng et al. High-performance single cell genetic analysis using microfluidic emulsion generator arrays, Anal. Chem. 82:3183-3190. (Year: 2010).*
Mensink et al. Quantitation of minimal residual disease in Philadelphia chromosome positive chronic myeloid leukaemia patients using real-time quantitative RT-PCR. British Journal of Haematology 102:768-774. (Year: 1998).*
U.S. Appl. No. 62/072,950, Weitz et al., Oct. 30, 2014.
U.S. Appl. No. 62/133,140, Weitz et al., Mar. 13, 2015.
International Search Report and Written Opinion for Application No. PCT/US2016/014531 dated Apr. 1, 2016.
International Preliminary Report on Patentability for Application No. PCT/US2016/014531 dated Aug. 8, 2017.
International Search Report and Written Opinion for Application No. PCT/US2016/022021 dated May 23, 2016.
International Preliminary Report on Patentability for Application No. PCT/US2016/022021 dated Sep. 28, 2017.
International Search Report and Written Opinion for Application No. PCT/US2017/028329 dated Jul. 26, 2017.
Alix-Panabières et al. Challenges in circulating tumour cell research. Nat Rev Cancer. Sep. 2014;14(9):623-31. doi: 10.1038/nrc3820. Epub Jul. 31, 2014.
Eastburn et al. Identification and genetic analysis of cancer cells with PCR-activated cell sorting. Nucleic Acids Res.2014;42(16):e128. doi: 10.1093/nar/gku606. Epub Jul. 16, 2014.
Oyola et al. Efficient depletion of host DNA contamination in malaria clinical sequencing. J Clin Microbiol. Mar. 2013;51(3):745-51. doi: 10.1128/JCM.02507-12. Epub Dec. 5, 2012.
Chinese Office Action for Application No. CN 201680027136.9 dated Feb. 21, 2019.
Chinese Office Action for Application No. CN 201680027136.9 dated Oct. 12, 2019.
Extended European Search Report for Application No. 16765491.2 dated Jul. 13, 2018.
European Office Action for Application No. 16765491.2 dated Nov. 18, 2019.
International Preliminary Report on Patentability for Application No. PCT/US2017/028329 dated Nov. 1, 2018.
Chinese Office Action for Application No. CN 201680015401.1 dated May 28, 2020.
Chinese Rejection Decision for Application No. CN 201680027136.9 dated Feb. 6, 2020.
Chang et al., Integrated polymerase chain reaction chips utilizing digital microfluidics. Biomed Microdevices. 2006;8(3):215-225.
Leamon et al., A massively parallel PicoTiterPlate based platform for discrete picoliter-scale polymerase chain reactions [published correction appears in Electrophoresis. Apr. 2004;25(7-8):1176]. Electrophoresis. 2003;24(21):3769-3777.
Margulies et al., Genome sequencing in microfabricated high-density picolitre reactors [published correction appears in Nature.

(56) References Cited

OTHER PUBLICATIONS

May 4, 2006;441(7089):120. Ho, Chun He corrected to Ho, Chun Heen]]. Nature. 2005;437(7057):376-380.

Oberholzer et al., Polymerase chain reaction in liposomes. Chem Biol. 1995;2(10):677-682.

Sepp et al., Microbead display by in vitro compartmentalization: selection for binding using flow cytometry. FEBS Lett. 2002;532(3):455-458.

Tawfik et al., Man-made cell-like compartments for molecular evolution. Nat Biotechnol. 1998;16(7):652-656.

Yan et al., Practical genetic disease diagnosis and prenatal diagnosis technology. Science and Technical Documentation Press. Jul. 21, 2014:98-99. Translation.

\* cited by examiner

DETERMINATION OF CELLS USING AMPLIFICATION

RELATED APPLICATIONS

This application is a national stage filing under 35 U.S.C. § 371 of International Application No. PCT/US2016/022021, filed Mar. 11, 2016, entitled "Determination of Cells Using Amplification," by Weitz et al., which claims the benefit of U.S. Provisional Patent Application Ser. No. 62/133,140, filed Mar. 13, 2015, entitled "Determination of Cells Using Amplification," by Weitz, et al., each of which is incorporated herein by reference in its entirety.

FIELD

The present invention generally relates to microfluidics and, in particular, to systems and methods for determining cells using amplification.

BACKGROUND

The determination of rare cells in samples, such as clinical samples, represents an unresolved and poorly addressed medical issue. These rare cells usually exist in the early stage of diseases and may result in serious consequences if not detected in a timely manner. Most traditional molecular biology techniques, such as real-time quantitative PCR, have limited sensitivity due to the presence of a large amount of background cells, inhibitors, noise, or the like. In addition, the cells in samples may be highly heterogeneous, such that bulk methods used for the detection of target cells at the population level are usually incapable of providing single-cell resolution or detection. Therefore, determining these significant rare cells individually, with sufficiently high sensitivity and specificity, remains challenging.

SUMMARY

The present invention generally relates to microfluidics and, in particular, to systems and methods for determining cells using amplification. The subject matter of the present invention involves, in some cases, interrelated products, alternative solutions to a particular problem, and/or a plurality of different uses of one or more systems and/or articles.

In one set aspect, the present invention is generally directed to a method. In one set of embodiments, the method includes acts of encapsulating cells within a plurality of microfluidic droplets; lysing at least some of the cells within the plurality of droplets to release nucleic acids from the cells into the interior of the droplets; within the interior of the droplets, applying conditions able to selectively amplify a target nucleic acid sequence suspected of being present within the nucleic acids released from the cells; combining the interiors of the droplets together to form a combined fluid; and determining amplified nucleic acids contained within the combined fluid.

In another set of embodiments, the method comprises, within a plurality of droplets encapsulating nucleic acids arising from a plurality of cells, applying conditions able to selectively amplify a target nucleic acid sequence suspected of being present within the nucleic acids; combining the interiors of the droplets together to form a combined fluid; and determining amplified nucleic acids contained within the combined fluid.

The method, in yet another set of embodiments, includes encapsulating cells within a plurality of droplets; lysing at least some of the cells within the plurality of droplets to release nucleic acids from the cells into the interior of the droplets; within the interior of the droplets, applying conditions able to selectively amplify a target nucleic acid sequence suspected of being present within the nucleic acids released from the cells; and determining amplified nucleic acids contained within the droplets.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to microfluidics and, in particular, to systems and methods for determining cells using amplification. In one set of embodiments, cells are encapsulated within droplets and nucleic acids from the cells amplified within the droplets. The droplets may then be pooled together and the amplified nucleic acids can be determined using PCR or other suitable techniques. In some embodiments, techniques such as these can be used to detect relatively rare cells that may be present, e.g., if the droplets are amplified using conditions able to selectively amplify nucleic acids arising from the relatively rare cells.

Figure 1:
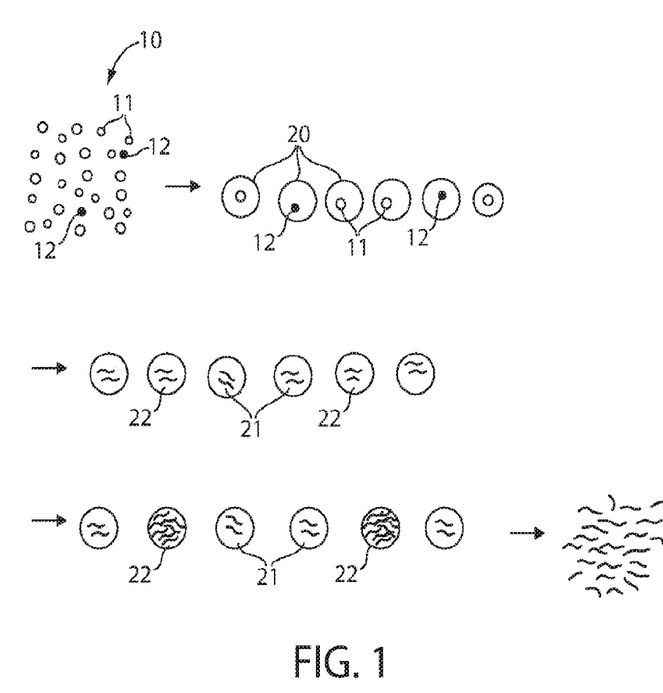
FIG. 1 illustrates cell amplification in accordance with one embodiment of the invention.

Referring to FIG. 1, one aspect of the invention is now discussed. However, in other embodiments, other systems and methods may be used as well, e.g., as described below. In FIG. 1, a population of cells 10 is shown. Most of the cells are of a first cell type 11 (or more than one cell type), while there are rare cells of a second type 12 that are contained within the population. It is these rare cells that are of primary interest, e.g., as target cells. As non-limiting examples, the first cells may be normal cells while the second cells may be cancerous or diseased cells, the first cells may be human cells while the second cells may be non-human cells (for example, pathogenic cells such as bacteria or the like), etc.

In some cases, the second (or target) cells may be quite rare within the overall population of cells. For example, only 1 out of 1,000, 10,000, 100,000, or 1,000,000 of the cells may be the second cell type, while the other cells may be of the first cell type. This rarity can cause problems in determining the second cell type under some circumstances. As an illustrative non-limiting example, many existing techniques for determining cells or nucleic acids in a population of cells have a false positive error rate. As an example, the error rate may be 1%, i.e., out of every 100 cells studied, one is erroneously positively identified (i.e., as a second cell type) when it should have been negatively identified (i.e., as a first cell type). However, even relatively low error rates (such as 1%) may still nonetheless be quite substantial compared to the rarity of the second cell type within the population. For instance, if there is only 1 second cell present for every 1,000 first cells in a population, then even a false positive error rate of 1% would still result in about 90% of all cells positively identified being incorrectly identified.

However, various embodiments as discussed herein can increase the ability to correctly determine rare cells within a population of cells. As a non-limiting illustrative example, as shown in FIG. 1, a population of cells 10 contains a first cell type 11 (or more than one type) and a second cell type 12. (As noted above, second cell type 12 may be exceedingly rare compared to first cell type 11 in certain embodiments, although such extreme ratios are not accurately depicted in FIG. 1 in the interests of clarity.) The population of cells may be encapsulated within a plurality of droplets 20, e.g., microfluidic droplets. The ratio of encapsulation may be 1:1 (i.e., one cell to one droplet), or any other suitable encapsulation ratio. (1:1 is also used here in the interests of clarity.)

Within the droplets, the cells may then be lysed in some fashion to release nucleic acids within the droplets, e.g., DNA and/or RNA from the cells may be released from the cells within the droplets. The lysing can be performed using any suitable technique for lysing cells. Non-limiting examples include ultrasound or exposure to suitable agents such as surfactants. In some cases, the exact technique chosen may depend on the type of cell being lysed; many such cell lysing techniques will be known by those of ordinary skill in the art.

Next, nucleic acids can be amplified within the droplets. Various techniques may be used to amplify the nucleic acid with the droplets, for example, PCR (polymerase chain reaction) techniques such as RT-PCR (reverse transcription polymerase chain reaction), or other techniques including those discussed herein. In certain embodiments, various PCR reagents may be added to the droplets (e.g., deoxyribonucleotides, primers, polymerases, reverse transcriptases, etc.), e.g., via injection or merging with other droplets, and/or the droplets may be subjected to conditions (such as temperature changes) to facilitate PCR amplification of nucleic acid with the droplets.

In some cases, the amplification conditions may be selected to amplify certain nucleic acids, relative to other nucleic acids, e.g., nucleic acids arising from the second cell types relative to the first cell types. For instance, as is shown in FIG. 1, nucleic acids 22 from cells 12 may be substantially amplified, relative to nucleic acids 21 from cells 11. Thus, as a non-limiting example, primers for PCR amplification may be selected so as to selectively amplify bacterial nucleic acids (or specific species of bacteria), relative to nucleic acids from human cells, e.g., to assist in the determination of bacteria within a sample. In some cases, relatively large amplifications may be achieved. For example, a nucleic acid may be amplified by at least about $10^3$, at least about $10^4$, at least about $10^5$, at least about $10^6$, or at least about $10^7$-fold within a droplet.

Containing individual cells in droplets may facilitate the amplification of desired or target nucleic acids (e.g., arising from the second cell types), relative to other nucleic acids (e.g., arising from the first cell types), at least in some embodiments. Since the droplets contain relatively few numbers of cells (for instance, zero or only one cell per droplet), there are fewer chances for competition reactions or other reactions, where undesired nucleic acids (e.g., from the first cell types) are amplified relative to the target nucleic acids (e.g., from the second cell types). Thus, the amplification of the second cell types may be enhanced by performing amplification within droplets, allowing for relatively rare nucleic acids within the population of nucleic acids to be substantially amplified relative to other nucleic acids within the population. In contrast, amplification of a population of different nucleic acids arising from different cells, i.e., without droplets, may result in competitive reactions, background cells, inhibitors, etc. that often can impede the amplification of the target nucleic acids.

After amplification, the interiors of the droplets may be merged or pooled together in some fashion. For example, the droplets may be "burst" or disrupted, for example, mechanically or by applying ultrasound, to release their contents, or the droplets may be coalesced together, for example, using suitable dipole moments or electric fields. The nucleic acids may thus be mixed together, e.g., into a common "pool," as is shown in FIG. 1. The population of nucleic acids (e.g., which may contain a greater population of target nucleic acids arising from the second cell types) may then be analyzed or determined in some fashion, qualitatively or quantitatively, for example, using techniques known to those of ordinary skill in the art. Examples of such techniques include digital PCR, qPCR, or other techniques as discussed herein. As nucleic acids arising from the second cell types may be substantially amplified, relative to the original population of cells, they may be easier to determine. Thus, for example, it could be concluded that the original population of cells contains (or does not contain) cancer cells, bacterial cells, or other target cells of interest.

The above discussion is a non-limiting example of one embodiment of the present invention that can be used to determine cells using amplification, e.g., within droplets. However, other embodiments are also possible. Accordingly, more generally, various aspects of the invention are directed to various systems and methods for determining cells using amplification.

As mentioned, certain aspects of the invention are generally directed to systems and methods of determining relatively rare cells within a population of cells. The population of cells may comprise one, or more than one, type of cell. The rare cells may, for example, be only 1 out of about 1,000, about 3,000, about 5,000, about 10,000, about 30,000, about 50,000 about 100,000, about 300,000, about 500,000, or about 1,000,000 of the cells contained within the population of cells. As non-limiting examples, the population of cells may be taken from a blood sample, a biopsy, a tissue sample, a tissue culture, a sample from another biological fluid (such as urine or sweat), or the like. As addition examples, the cells may also be taken from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. The rare cells may be, for example, cancer cells, or pathogens such as bacteria that are present in the sample (e.g., which may cause a disease in a subject), or the like. Thus, as a non-limiting example, in one embodiment, blood may be taken from a subject (such as a human subject), and analyzed to determine tumor cells (e.g., leukemia or other cancer cells) contained within the blood. As another non-limiting example, blood may be taken from a subject (such as a human subject) may be analyzed to determine pathogens such as bacteria that may be present.

In some cases, the cells may be encapsulated within a plurality of droplets, such as microfluidic droplets. Various techniques for creating or manipulating droplets are known; non-limiting examples include those in Int. Pat. Apl. Pub. No. WO 2004/091763, entitled "Formation and Control of Fluidic Species," by Link et al.; Int. Pat. Apl. Pub. No. WO 2004/002627, entitled "Method and Apparatus for Fluid Dispersion," by Stone et al.; Int. Pat. Apl. Pub. No. WO 2006/096571, entitled "Method and Apparatus for Forming Multiple Emulsions," by Weitz et al.; Int. Pat. Apl. Pub. No. WO 2005/021151, entitled "Electronic Control of Fluidic Species," by Link et al.; Int. Pat. Apl. Pub. No. WO 2011/056546, entitled "Droplet Creation Techniques," by Weitz, et al., each incorporated herein by reference in its entirety.

The cells may be encapsulated in the droplets at any suitable average ratio. For example, in one set of embodiments, the cells are encapsulated at about a 1:1 ratio, e.g., at an average of about 1 cell per droplet. However, in some cases, lower ratios of cells per droplet may be desired. For instance, the ratio may be less than about 1:10, less than about 1:30, less than about 1:50, less than about 1:100, less than about 1:300, less than about 1:500, less than about 1:1,000, less than about 1:3,000, less than about 1:500, less than about 1:10,000, less than about 1:30,000, less than about 1:50,000, less than about 1:100,000, less than about 1:300,000, less than about 1:500,000, less than about 1:000,000, or any other suitable average ratio of cells to droplets. Such ratios may be useful, for example, to ensure that most of the droplets encapsulate either zero or one cell, and thereby limit the number of droplets containing two or more cells. However, in some embodiments, average ratios higher than 1:1 may also be used, e.g., at least about 2:1, at least about 3:1, at least about 5:1, at least about 10:1, at least about 50:1, at least about 100:1 of cells to droplets, etc.

After encapsulation, the cells may be lysed within the droplets, e.g., to release nucleic acids into the interiors of the droplets. As non-limiting examples, the cells within the droplets may be exposed to a lysing chemical (e.g., pure water, a surfactant such as Triton-X or SDS, an enzyme such as lysozyme, lysostaphin, zymolase, cellulase, mutanolysin, glycanases, proteases, mannase, etc.), or a physical condition (e.g., ultrasound, ultraviolet light, mechanical agitation, etc.). Lysing chemicals may be added, for example, by merging the droplets with other droplets containing lysing chemicals, through injection techniques, or the like, for instance as discussed herein. See also Int. Pat. Apl. Pub. No. WO 2010/151776, incorporated herein by reference in its entirety.

In some embodiments, nucleic acids within the droplets may be tagged or "barcoded," e.g., joined to other nucleic acids that can be used to uniquely identify the nucleic acids. However, this is optional and in other embodiments, no barcoding step is required. In some embodiments, one or more "tags" may be present within or added to a droplet, which can be analyzed or used, for instance, to determine the identity and/or history of the droplet, to determine cells within the droplets, to determine nucleic acids within the droplet, or the like. In some cases, the tags may be chosen to be relatively inert relative to other components of the droplet. The tags may be present initially in the droplet, and/or subsequently added. For instance, tags may be added when the droplet is exposed to one or more conditions (or proximate in time to such exposure). In some cases, more than one tag may be present in a droplet. Non-limiting examples of tagging or barcoding are discussed in U.S. Pat. Apl. Ser. No. 61/981,123, entitled "Systems and Methods for Droplet Tagging," by Bernstein, et al., filed Apr. 17, 2014; U.S. Pat. Apl. Ser. No. 61/981,108, entitled "Methods and Systems for Droplet Tagging and Amplification," by Weitz, et al., filed Apr. 17, 2014; or U.S. Pat. Apl. Ser. No. 62/072,950, entitled "Methods and Systems for Barcoding Nucleic Acids using Transposons," each incorporated herein by reference in its entirety.

After release, the nucleic acids may be amplified within the droplets in any suitable fashion. Non-limiting examples of suitable techniques include PCR (polymerase chain reaction) or other amplification techniques. Typically, in PCR, the nucleic acids are heated to cause dissociation of the nucleic acids into single strands, and a heat-stable DNA polymerase (such as Taq polymerase) is used to amplify the nucleic acid. This process is often repeated multiple times to amplify the nucleic acids.

Thus, in one set of embodiments, PCR may be performed within the droplets. For example, the droplets may contain a polymerase (such as Taq polymerase), and DNA nucleotides, and the droplets may be processed (e.g., via repeated heated and cooling) to amplify the nucleic acid within the droplets. The polymerase and nucleotides may be added at any suitable point, e.g., before, during, or after release of nucleic acids from cells within the droplets. For instance, as a non-limiting example, a droplet containing polymerase or DNA nucleotides may be fused to a droplet containing nucleic acids (e.g., arising from a cell) to allow amplification of the nucleic acids to occur, and/or injection techniques may be used to introduce polymerase or DNA nucleotides. Those of ordinary skill in the art will be aware of suitable PCR techniques and variations, such as assembly PCR or polymerase cycling assembly, which may be used in some embodiments to produce an amplified nucleic acid.

The nucleic acids may be amplified to any suitable extent. The degree of amplification may be controlled, for example, by controlling factors such as the temperature, cycle time, or amount of enzyme and/or deoxyribonucleotides contained within the droplets. For instance, in some embodiments, a population of droplets may have at least about 10,000, at least about 30,000, at least about 50,000, at least about 100,000, at least about 150,000, at least about 200,000, at least about 250,000, at least about 300,000, at least about 400,000, at least about 500,000, at least about 750,000, at least about 1,000,000 or more molecules of the amplified nucleic acid per droplet. In some embodiments, the nucleic acids may be amplified by at least about $10^3$-, at least about $10^4$-, at least about $10^5$-, at least about $10^6$-, or at least about $10^7$-fold within a droplet.

In addition, suitable primers may be used to initiate polymerization, e.g., P5 and P7, or other primers known to those of ordinary skill in the art. In some embodiments, primers may be added to the droplets, or the primers may be present on one or more of the nucleic acids within the droplets. Those of ordinary skill in the art will be aware of suitable primers, many of which can be readily obtained commercially.

In one set of embodiments, the primers are chosen on the basis of their ability to selectively amplify certain types of nucleic acids, relative to other types of nucleic acids. For example, the primer may selectively bind to and allow amplification of nucleic acids arising from a target cell, relative to other nucleic acids from other cells that may be present in a population of cells. The primers can be chosen on their ability to bind to DNA or RNA (for example, mRNA) that may be present within the cells. The primers may, for example, arise from human cells or non-human cells, e.g., bacterial cells, depending on the application. The primers may also be specific to one cell or one type of cell, or the primers may be non-specific, or specific to a class or type of cell. For instance, the primer may be include non-specific bacterial primers that are generally able to recognize nucleic acids from more than one species of bacteria. In addition, more than one type of primer may be used in certain embodiments. For example, in one set of embodiments, a plurality of primers able to bind bacteria, cancer cells, or the like may be used, e.g., to facilitate amplification of nucleic acids arising from those cells, relative to other cells in the population. Many such primer "kits" can be obtained commercially.

In some embodiments, various PCR reagents may be added to the droplets (e.g., deoxyribonucleotides, primers, polymerases, reverse transcriptases, etc.), e.g., via injection or merging with other droplets, e.g., as discussed herein. In some cases, at least some of the PCR reagents may be added using other techniques, or at least some of the PCR reagents may be present within the droplets at formation (e.g., when the cells are encapsulated within the droplets. Techniques for merging or coalescing droplets or injecting a fluid into a droplet are known to those of ordinary skill in the art, and include those techniques discussed herein. See, for example, U.S. Pat. Apl. Pub. No. 2012-0132288, entitled "Fluid Injection," by Weitz, et al., Int. Pat. Apl. Pub. No. WO 2004/091763, entitled "Formation and Control of Fluidic Species," by Link et al.; Int. Pat. Apl. Pub. No. WO 2004/002627, entitled "Method and Apparatus for Fluid Dispersion," by Stone et al., Int. Pat. Apl. Pub. No. WO 2005/021151, entitled "Electronic Control of Fluidic Species," by Link et al.; Int. Pat. Apl. Pub. No. WO 2011/056546, entitled "Droplet Creation Techniques," by Weitz, et al., each incorporated herein by reference in its entirety.

In addition, in some embodiments, the droplets may be subjected to temperature changes and/or other conditions in order to facilitate PCR amplification of nucleic acid with the droplets. For example, in PCR reactions, the nucleic acids may be heated (e.g., to a temperature of at least about 50° C., at least about 70° C., or least about 90° C. in some cases) to cause dissociation of the nucleic acids into single strands, and a heat-stable DNA polymerase (such as Taq polymerase) is used to amplify the nucleic acid. This process is often repeated multiple times to amplify the nucleic acids. Those of ordinary skill in the art will be aware of a variety of different PCR techniques that may be used, such as RT-PCR.

After amplification, the interiors of the droplets may be merged or pooled together in some fashion. For example, in some embodiments, the droplets may be disrupted (or "broken") using techniques such as mechanical disruption, chemical disruption (for example, suitable surfactants), and/or ultrasound, e.g., to release their contents. In another set of embodiments, the droplets may be merged or coalesced together, for example, using dipole moments or electric fields. See, e.g., U.S. patent application Ser. No. 11/698,298, filed Jan. 24, 2007, entitled "Fluidic Droplet Coalescence," by Ahn, et al., published as U.S. Patent Application Publication No. 2007/0195127 on Aug. 23, 2007, incorporated herein by reference in its entirety. For example, two droplets can be given opposite electric charges (i.e., positive and negative charges, not necessarily of the same magnitude), which can increase the electrical interaction of the two droplets such that fusion or coalescence of the droplets can occur due to their opposite electric charges. For instance, an electric field may be applied to the droplets, the droplets may be passed through a capacitor, a chemical reaction may cause the droplets to become charged, etc. In some embodiments, if the droplets are electrically charged with opposite charges (which can be, but are not necessarily of, the same magnitude), the droplets may be able to fuse or coalesce. As another example, the droplets may not necessarily be given opposite electric charges (and, in some cases, may not be given any electric charge), and are fused through the use of dipoles induced in the droplets that causes the droplets to coalesce.

After combination, the nucleic acids that are collected together may be analyzed or determined using any methods known to those of ordinary skill in the art. For instance, in some embodiments, the presence (or absence) of nucleic acids arising from relatively rare target cells may be determined. In some cases, the concentration may be determined, e.g., to determine the relative amount or percentage of the target cells in the initial population. The nucleic acids may also be sequenced in some embodiments. A variety of techniques may be used, for example, sequencing techniques such as chain-termination sequencing, sequencing-by-hybridization, Maxam-Gilbert sequencing, dye-terminator sequencing, chain-termination methods, Massively Parallel Signature Sequencing (Lynx Therapeutics), polony sequencing, pyrosequencing, sequencing by ligation, ion semiconductor sequencing, DNA nanoball sequencing, single-molecule real-time sequencing, nanopore sequencing, microfluidic Sanger sequencing, digital RNA sequencing ("digital RNA-seq"), etc.

Additional details regarding systems and methods for manipulating droplets in a microfluidic system follow, in accordance with certain aspects of the invention. For example, various systems and methods for screening and/or sorting droplets are described in U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007, incorporated herein by reference. As a non-limiting example, in some aspects, by applying (or removing) a first electric field (or a portion thereof), a droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc.

As mentioned, certain embodiments comprise a droplet contained within a carrying fluid. For example, there may be a first phase forming droplets contained within a second phase, where the surface between the phases comprises one or more proteins. For example, the second phase may comprise oil or a hydrophobic fluid, while the first phase may comprise water or another hydrophilic fluid (or vice versa). It should be understood that a hydrophilic fluid is a fluid that is substantially miscible in water and does not show phase separation with water at equilibrium under ambient conditions (typically 25° C. and 1 atm). Examples of hydrophilic fluids include, but are not limited to, water and other aqueous solutions comprising water, such as cell or biological media, ethanol, salt solutions, saline, blood, etc. In some cases, the fluid is biocompatible.

Similarly, a hydrophobic fluid is one that is substantially immiscible in water and will show phase separation with water at equilibrium under ambient conditions. As previously discussed, the hydrophobic fluid is sometimes referred to by those of ordinary skill in the art as the "oil phase" or simply as an oil. Non-limiting examples of hydrophobic fluids include oils such as hydrocarbons oils, silicon oils, fluorocarbon oils, organic solvents, perfluorinated oils, perfluorocarbons such as perfluoropolyether, etc. Additional examples of potentially suitable hydrocarbons include, but are not limited to, light mineral oil (Sigma), kerosene (Fluka), hexadecane (Sigma), decane (Sigma), undecane (Sigma), dodecane (Sigma), octane (Sigma), cyclohexane (Sigma), hexane (Sigma), or the like. Non-limiting examples of potentially suitable silicone oils include 2 cst polydimethylsiloxane oil (Sigma). Non-limiting examples of fluorocarbon oils include FC3283 (3M), FC40 (3M), Krytox GPL (Dupont), etc. In addition, other hydrophobic entities may be contained within the hydrophobic fluid in some embodiments. Non-limiting examples of other hydrophobic entities include drugs, immunologic adjuvants, or the like.

Thus, the hydrophobic fluid may be present as a separate phase from the hydrophilic fluid. In some embodiments, the hydrophobic fluid may be present as a separate layer, although in other embodiments, the hydrophobic fluid may be present as individual fluidic droplets contained within a continuous hydrophilic fluid, e.g. suspended or dispersed within the hydrophilic fluid. This is often referred to as an oil/water emulsion. The droplets may be relatively monodisperse, or be present in a variety of different sizes, volumes, or average diameters. In some cases, the droplets may have an overall average diameter of less than about 1 mm, or other dimensions as discussed herein. In some cases, a surfactant may be used to stabilize the hydrophobic droplets within the hydrophilic liquid, for example, to prevent spontaneous coalescence of the droplets. Non-limiting examples of surfactants include those discussed in U.S. Pat. Apl. Pub. No. 2010/0105112, incorporated herein by reference. Other non-limiting examples of surfactants include Span80 (Sigma), Span80/Tween-20 (Sigma), Span80/Triton X-100 (Sigma), Abil EM90 (Degussa), Abil we09 (Degussa), polyglycerol polyricinoleate "PGPR90" (Danisco), Tween-85, 749 Fluid (Dow Corning), the ammonium carboxylate salt of Krytox 157 FSL (Dupont), the ammonium carboxylate salt of Krytox 157 FSM (Dupont), or the ammonium carboxylate salt of Krytox 157 FSH (Dupont). In addition, the surfactant may be, for example, a peptide surfactant, bovine serum albumin (BSA), or human serum albumin.

The droplets may have any suitable shape and/or size. In some cases, the droplets may be microfluidic, and/or have an average diameter of less than about 1 mm. For instance, the droplet may have an average diameter of less than about 1 mm, less than about 700 micrometers, less than about 500 micrometers, less than about 300 micrometers, less than about 100 micrometers, less than about 70 micrometers, less than about 50 micrometers, less than about 30 micrometers, less than about 10 micrometers, less than about 5 micrometers, less than about 3 micrometers, less than about 1 micrometer, etc. The average diameter may also be greater than about 1 micrometer, greater than about 3 micrometers, greater than about 5 micrometers, greater than about 7 micrometers, greater than about 10 micrometers, greater than about 30 micrometers, greater than about 50 micrometers, greater than about 70 micrometers, greater than about 100 micrometers, greater than about 300 micrometers, greater than about 500 micrometers, greater than about 700 micrometers, or greater than about 1 mm in some cases. Combinations of any of these are also possible; for example, the diameter of the droplet may be between about 1 mm and about 100 micrometers. The diameter of a droplet, in a non-spherical droplet, may be taken as the diameter of a perfect mathematical sphere having the same volume as the non-spherical droplet.

In some embodiments, the droplets may be of substantially the same shape and/or size (i.e., "monodisperse"), or of different shapes and/or sizes, depending on the particular application. In some cases, the droplets may have a homogenous distribution of cross-sectional diameters, i.e., in some embodiments, the droplets may have a distribution of average diameters such that no more than about 20%, no more than about 10%, or no more than about 5% of the droplets may have an average diameter greater than about 120% or less than about 80%, greater than about 115% or less than about 85%, greater than about 110% or less than about 90%, greater than about 105% or less than about 95%, greater than about 103% or less than about 97%, or greater than about 101% or less than about 99% of the average diameter of the microfluidic droplets. Some techniques for producing homogenous distributions of cross-sectional diameters of droplets are disclosed in International Patent Application No. PCT/US2004/010903, filed Apr. 9, 2004, entitled "Formation and Control of Fluidic Species," by Link, et al., published as WO 2004/091763 on Oct. 28, 2004, incorporated herein by reference. In addition, in some instances, the coefficient of variation of the average diameter of the droplets may be less than or equal to about 20%, less than or equal to about 15%, less than or equal to about 10%, less than or equal to about 5%, less than or equal to about 3%, or less than or equal to about 1%. However, in other embodiments, the droplets may not necessarily be substantially monodisperse, and may instead exhibit a range of different diameters.

Those of ordinary skill in the art will be able to determine the average diameter of a population of droplets, for example, using laser light scattering or other known techniques. The droplets so formed can be spherical, or non-spherical in certain cases. The diameter of a droplet, in a non-spherical droplet, may be taken as the diameter of a perfect mathematical sphere having the same volume as the non-spherical droplet.

In some embodiments, one or more droplets may be created within a channel by creating an electric charge on a fluid surrounded by a liquid, which may cause the fluid to separate into individual droplets within the liquid. In some embodiments, an electric field may be applied to the fluid to cause droplet formation to occur. The fluid can be present as a series of individual charged and/or electrically inducible droplets within the liquid. Electric charge may be created in the fluid within the liquid using any suitable technique, for example, by placing the fluid within an electric field (which may be AC, DC, etc.), and/or causing a reaction to occur that causes the fluid to have an electric charge.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. Techniques for producing a suitable electric field (which may be AC, DC, etc.) are known to those of ordinary skill in the art. For example, in one embodiment, an electric field is produced by applying voltage across a pair of electrodes, which may be positioned proximate a channel such that at least a portion of the electric field interacts with the channel. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In some cases, the channel dimensions may be altered with respect to time (for example, mechanically or electromechanically, pneumatically, etc.) in such a manner as to cause the formation of individual droplets to occur. For example, the channel may be mechanically contracted ("squeezed") to cause droplet formation, or a fluid stream may be mechanically disrupted to cause droplet formation, for example, through the use of moving baffles, rotating blades, or the like.

Some embodiments of the invention generally relate to systems and methods for fusing or coalescing two or more droplets into one droplet, e.g., where the two or more droplets ordinarily are unable to fuse or coalesce, for example, due to composition, surface tension, droplet size, the presence or absence of surfactants, etc. In certain cases, the surface tension of the droplets, relative to the size of the droplets, may also prevent fusion or coalescence of the droplets from occurring.

As a non-limiting example, two droplets can be given opposite electric charges (i.e., positive and negative charges, not necessarily of the same magnitude), which can increase the electrical interaction of the two droplets such that fusion or coalescence of the droplets can occur due to their opposite electric charges. For instance, an electric field may be applied to the droplets, the droplets may be passed through a capacitor, a chemical reaction may cause the droplets to become charged, etc. The droplets, in some cases, may not be able to fuse even if a surfactant is applied to lower the surface tension of the droplets. However, if the droplets are electrically charged with opposite charges (which can be, but are not necessarily of, the same magnitude), the droplets may be able to fuse or coalesce. As another example, the droplets may not necessarily be given opposite electric charges (and, in some cases, may not be given any electric charge), and are fused through the use of dipoles induced in the droplets that causes the droplets to coalesce. Also, the two or more droplets allowed to coalesce are not necessarily required to meet "head-on." Any angle of contact, so long as at least some fusion of the droplets initially occurs, is sufficient. See also, e.g., U.S. patent application Ser. No. 11/698,298, filed Jan. 24, 2007, entitled "Fluidic Droplet Coalescence," by Ahn, et al., published as U.S. Patent Application Publication No. 2007/0195127 on Aug. 23, 2007, incorporated herein by reference in its entirety.

In one set of embodiments, a fluid may be injected into a droplet. The fluid may be microinjected into the droplet in some cases, e.g., using a microneedle or other such device. In other cases, the fluid may be injected directly into a droplet using a fluidic channel as the droplet comes into contact with the fluidic channel. Other techniques of fluid injection are disclosed in, e.g., International Patent Application No. PCT/US2010/040006, filed Jun. 25, 2010, entitled "Fluid Injection," by Weitz, et al., published as WO 2010/151776 on Dec. 29, 2010; or International Patent Application No. PCT/US2009/006649, filed Dec. 18, 2009, entitled "Particle-Assisted Nucleic Acid Sequencing," by Weitz, et al., published as WO 2010/080134 on Jul. 15, 2010, each incorporated herein by reference in its entirety.

The following documents are incorporated herein by reference in their entirety for all purposes: U.S. Pat. Apl. Ser. No. 62/106,981, entitled "Systems, Methods, and Kits for Amplifying or Cloning Within Droplets," by Weitz, et al.; U.S. Pat. Apl. Pub. No. 2010-0136544, entitled "Assay and Other Reactions Involving Droplets," by Agresti, et al.; Int. Pat. Apl. Pub. No. WO 2004/091763, entitled "Formation and Control of Fluidic Species," by Link et al.; Int. Pat. Apl. Pub. No. WO 2004/002627, entitled "Method and Apparatus for Fluid Dispersion," by Stone et al.; Int. Pat. Apl. Pub. No. WO 2006/096571, entitled "Method and Apparatus for Forming Multiple Emulsions," by Weitz et al.; Int. Pat. Apl. Pub. No. WO 2005/021151, entitled "Electronic Control of Fluidic Species," by Link et al.; Int. Pat. Apl. Pub. No. WO 2011/056546, entitled "Droplet Creation Techniques," by Weitz, et al.; Int. Pat. Apl. Pub. No. WO 2010/033200, entitled "Creation of Libraries of Droplets and Related Species," by Weitz, et al.; U.S. Pat. Apl. Pub. No. 2012-0132288, entitled "Fluid Injection," by Weitz, et al.; Int. Pat. Apl. Pub. No. WO 2008/109176, entitled "Assay And Other Reactions Involving Droplets," by Agresti, et al.; Int. Pat. Apl. Pub. No. WO 2010/151776, entitled "Fluid Injection," by Weitz, et al.; U.S. Pat. Apl. Ser. No. 61/981,123, entitled "Systems and Methods for Droplet Tagging," by Bernstein, et al.; U.S. Pat. Apl. Ser. No. 61/981,108, entitled "Methods and Systems for Droplet Tagging and Amplification," by Weitz, et al.; and Int. Pat. Apl. Pub. No. PCT/US2014/037962, filed May 14, 2014, entitled "Rapid Production of Droplets," by Weitz, et al.

Also incorporated herein by reference in its entirety is U.S. Provisional Patent Application Ser. No. 62/133,140, filed Mar. 13, 2015, entitled "Determination of Cells Using Amplification," by Weitz, et al.

The following examples are intended to illustrate certain embodiments of the present invention, but do not exemplify the full scope of the invention.

Example 1

This example demonstrates a two-step drop-based amplification strategy to overcome detection errors often seen in other amplification methods, in accordance with some embodiments of the invention. In the first-step, single cells are encapsulated in droplets (e.g., microfluidic droplets), and amplification of nucleic acids is performed within the droplets. This amplification procedure is similar to other amplification techniques, but the goal is to amplify the targets from a single cell rather than actual detection. The resulting PCR amplicons or amplified nucleic acid are then pooled together, and used as a template for the second-step, which includes determination of the amplified nucleic acids, e.g., by digital PCR, counting, etc. Expanding the original single cell by a high degree (for example, about $10^3$ to $10^7$ amplicons per target gene) results in several potential advantages, including statistically-valid results, noise reduction, or the ability to divide the sample into different portions (e.g., for different subsequent analyses), e.g., without losing the coverage.

This example demonstrates an application of this two-step drop-based amplification strategy to detect and quantify very rare drug-resistance cells carrying PLCG1 mutations from a leukemia patient's blood. As estimated by a mathematic model, the mutation rate is around one in a million. Mutation-specific primers were designed and used to first amplify PLCG1 genes in both mutant and wild-type cells in bulk. By running agarose gel electrophoresis, it was observed that only PLCG1 gene in mutant cells could be amplified. The cells were then encapsualted into drops with lysis buffer, followed by injecting RT-PCR reagent and RT-PCR. In the drop detection results of the mutant cells, two populations were observed: one with low fluorescence intensity indicates the empty drops, and the other with high fluorescence intensity indicates the drops containing PLCG1 mutant cells. In the wild-type cell sample, 0.1% bright drops were observed, even though in theory, no bright drops should have been observed Therefore, after the first-step of amplification, it would not be possible to accurately quantify mutant cells if the mutation rate is one in a million.

All of the amplicons were polled together, and a second-step gene-specific digital PCR was performed. The drops in which amplification occur contained about $10^7$ amplicons, while the "noise" drops contained unspecific amplicons or nothing, so the difference between mutant and wild-type cells has been enlarged from 1:0 to $10^7$:0. Thus, these results are more statistically significant, rather than stochastic. To be able to accurately quantify the number of mutant cells, a serial dilution was prepared by mixing the mutant and wild-type cells at different ratios down to $1:10^6$. After two-step amplification, a standard curve was established and used to observe a linear correlation between the dilution factor and cell number. Using this standard curve, mutant cells in real clinical samples could be quantified.

Example 2

This example evaluates antimicrobial drug efficacy in patients with infectious diseases. One of the most important markers for studying their efficacy is gene up-regulation or down-regulation. By comparing the expression level (mRNA) of certain genes in the presence or absence of drugs, the effectiveness of the drug on a microbe can be determined.

However, in the detection of certain gene expression, early stage gene expression of infection pathogen concentration is usually very low, and mRNA in bacteria is also very low, about 10 mRNAs per gene. In addition, the primers that should be used for amplification often aren't known because it is not known which pathogen exists in a sample, out of many possible pathogen candidates. However, in this example, all pathogen candidate primers are first used to amplify all candidate bacteria mRNA fragments in the sample, and then the samples are divided and digital PCR mixtures prepared for individual candidates for detection. In some cases, each digital PCR mixture can be barcoded, e.g., with fluorescence dye, for simultaneous detection.

Example 3

Following are example material and methods useful for certain embodiments of the invention.

Detection of rare mutant cells with the presence of host cells. Preparation of cells expressing mutant and wild-type target gene. A stable mouse leukemia cell line, 30019, that expresses wild-type and mutant Phospholipase C (PLCG-1) gene were maintained in RPMI-1640 supplemented with 10% low-endotoxin fetal calf serum, 100 U penicillin/ml, 100 micrograms/ml streptomycin, 15 micrograms/ml gentamycin, 1% glutamine, $50 \times 10^{-6}$ M 2-mercaptoethanol, and 1000 ng/ml G418. These cells were harvested and counted before they were co-flowed into the microfluidic device for single-cell analysis. The 30019 cells were mixed with white blood cells at 1:1,000, 1:10,000, 1:100,000, and 1:1,000,000 ratios, respectively.

Preparation of microfluidic devices. Polydimethylsiloxane (PDMS) microfluidic devices were fabricated using standard soft lithographic methods. The microfluidic channel walls are rendered hydrophobic by treating them with Aquapel (PPG, Pittsburgh, Pa.).

Preparation of a 2× cell lysis buffer and a 2×RT-PCR cocktail. The cell lysis buffer contained 1 M Tris-HCl pH 8.0, 10% Tween 20, 100 mg/ml proteinase K and 2,000 U/ml DNase I. Primers for amplifying Phospholipase C (PLCG-1) gene were bought from IDT, which were F-5'-GGGTAAGTGGCATGAGCAAGAAAGAACC-3' and R-5'-TTTCTGCGCTTTGTGG TTTATGAA-3'. The Taqman probe was purchased from Life Tech, and its sequence was 5'-FAM-ACACAGGAGAAGGTGACATTT-GAA-3'-MGB. The 50 microliter 2×RT-PCR cocktails contained 4 microliters of OneStep RT-PCR enzyme mixed with 2× OneStep RT-PCR buffer from Qiagen, 800 micromolar dNTPs, 0.6 micromolar forward and reverse primers, 0.5 micromolar Taqman probe, 0.4 microgram/microliter BSA, and 0.4% Tween 20.

Generation of monodisperse aqueous drops containing cells and lysis of cells. A microfluidic chip was used that contained a co-flow drop maker with a cross section of 35 micrometer$^2$ to generate 50 micrometer (diameter) monodisperse aqueous drops in fluorinated oil, HFE-7500 (3M, Saint Paul, Minn., U.S.A), containing 2% (w/w) Krytox-PEG diblock co-polymer surfactant (RAN Biotech, Beverly, Mass.). The cell lysis buffer and different cell mixtures were encapsulated in drops via co-flow in different channels at a 1:1 ratio. The drops were collected in a PCR tube and covered with mineral oil. To lyse the cells within these drops, the following protocol was used: 37° C. for 10 min, 50° C. for 20 min, 70° C. for 10 min, then the drops containing lysed cells were kept on ice.

Picoinjection of 2×RT-PCR reagent and RT-PCR. The drops containing lysed cells were flowed into a microfluidic pico-injection device and a 2×RT-PCR cocktail was injected into the drop by electro-coalescence. See, e.g., U.S. Pat. Apl. Pub. No. 2012/0132288, incorporated herein by reference in its entirety. The drops were spaced on chip by oil with 2% w/w surfactant. The device electrodes were connected to a high voltage TREK 2210 amplifier (TREK, Lockport, N.Y.) which supplied a 100 V sine wave at a frequency of 25 kHz. The flow rate of the PCR cocktail was chosen to ensure that the buffer was added at ~1:1 ratio upon coalescence. Typical flow rates fulfilling these requirements were 300 microliters/hr for the oil, 60 microliters/hr for the barcode primer-drops, and 30 microliters/hr for the PCR cocktail. The drops were collected in PCR tubes and covered with mineral oil to prevent evaporation. The following RT-PCR protocol was used: 50° C. for 30 min, 95° C. for 10 min, 2 cycles of 94° C. for 15 s, 64° C. for 8 min, and 38 cycles of 95° C. for 15 s, 62° C. for 1 min.

Second-round digital PCR. To obtain the templates for the second-round digital PCR, 25 microliters of 1H,1H,2H,2H-perfluoro-1-octanol (PFO; Sigma-Aldrich, St. Louis, Mo.) was added to the emulsion and gently centrifuged to separate the phases. PCR products from the first-round RT-PCR were all in the liquid phase. The PCR products were diluted by 1,000 fold and used for the second-round digital PCR. The 25 microliter PCR cocktail contained 1 microliter of OneStep RT-PCR enzyme mix with 1× OneStep RT-PCR buffer from Qiagen, 400 micromolar dNTPs, 0.25 micromolar forward and reverse primers, 0.24 micromolar Taqman probe, 0.2 micrograms/microliter BSA, 0.2% Tween 20, and 1 microliter of diluted PCR products. A microfluidic device containing a flow-focusing drop maker with a cross section of 15 micrometers×25 micrometers was used to generate 25 micrometer monodisperse aqueous drops in HFE-7500 containing 2% (w/w) surfactant. The flow was driven by applying a −0.4 psi vacuum at the outlet (1 psi=6895 Pa). The drops were collected in a PCR tube and covered with mineral oil to prevent evaporation. The following RT-PCR protocol was used: 95° C. for 10 min, 40 cycles of 2 cycles of 94° C. for 15 s, 64° C. for 8 min, and 38 cycles of 95° C. for 15 s, 62° C. for 1 min.

Fluorescence detection of drops after second-round digital PCR. After amplification the drops were re-injected into the microfluidic reading and sorting device. To achieve a stream of evenly spaced drops for detection, flows were combined from the drops and HFE-7500 oil with 1% surfactant in a "T" junction, where the flow rate of the drops was 15 microliters/h and that of the oil was 180 microliters/h. This stream flowed through a 25 micrometer×25 micrometer channel, and as the drops passed the focal point of an excitation laser (488 nm), their fluorescence was collected by a microscope objective and focused onto a photomultiplier tube (PMT) from Hammamatsu. The pulses were acquired by a real-time field-programmable gate array card from National Instruments and recorded by a LabView program and analyzed using a MATLAB code. The pulse height was used as a measure of drop fluorescence. The pulse width, which was the duration of time for a drop to pass through the laser, was used as a measure of drop size. The sensitivity of the PMT was sufficiently high to detect drops not containing target templates, due to the intrinsic fluorescence of the Taqman probe.

Quantification of mutant cells in the sample. To quantify the mutant cells in the original sample, the fluorescence detection results from these cell mixture samples were used to establish a standard curve. The X axis was the number of the mutant cells in the cell mixture, and the Y axis was the number of bright drops after second-round digital PCR. When the mutant cells in an unknown sample were quantified, first-round RT-PCR and second-round PCR were performed to get the number of bright drops, thereby obtaining the corresponding number of the mutant cells.

Evaluation of antimicrobial drug efficacy in patients with infectious diseases. Purify bacteria RNA from blood. Bacteria RNAs were purified from blood with and without antibiotic treatment using a Qiagen blood RNA kit, with some modification. Briefly, protection buffer was added to prevent the bacteria expression profile from being changed during the purification procedure. Then, the red blood cells were lysed and centrifuged to collect the bacteria and white blood cells. To lyse the bacteria and white blood cells, proteinase K was added to the cell pellet and incubated at room temperature for 10 min, followed by adding RLT lysis buffer in the kit. The addition of proteinase K also prevented the bacteria RNA from being digested by cellular RNase. The cell lysate was loaded onto a Qiagen Column, so that the RNA could bind to the silicon membrane. After two steps of washing, the RNA was eluted into DEPC water and frozen at −80° C.

First-round digital RT-PCR. A 25 microliter PCR cocktail containing 1 microliter of OneStep RT-PCR enzyme was mixed with 1× OneStep RT-PCR buffer from Qiagen, 400 micromolar dNTPs, 0.01 micromolar each forward and reverse primers for amplifying total 48 different bacteria, 0.24 micromolar Taqman probe, 0.2 microgram/microliter BSA, 0.2% Tween 20, and 5 microliter of purified bacteria RNA. A microfluidic device containing a flow-focusing drop maker with a cross section of 25 micrometer×25 micrometer was used to generate 35 micrometer monodisperse aqueous drops in HFE-7500 containing 2% (w/w) surfactant. The flow was driven by applying a −0.4 psi vacuum at the outlet. The drops were collected in a PCR tube and covered with mineral oil to prevent evaporation. The following RT-PCR protocol was used: 50° C. for 20 min, 95° C. for 10 min, 40 cycles of 95° C. for 30 s, 60° C. for 5 min and 72° C. 1 min.

Second-round multiplex digital PCR to quantify the bacteria mRNA. To obtain the templates for the second-round digital PCR, 25 microliters of 1H,1H,2H,2H-perfluoro-1-octanol (PFO; Sigma-Aldrich, St. Louis, Mo.) was added to the emulsion and gently centrifuged to separate the phases. PCR products from the first-round RT-PCR were all in the liquid phase. In total, there were 48 PCR cocktails for 48 different genes which belong to 48 different bacteria. Each 25 microliter PCR cocktail contained 1 microliter of OneStep RT-PCR enzyme mixed with 1× OneStep RT-PCR buffer from Qiagen, 400 micromolar dNTPs, 0.25 micromolar each forward and reverse primers, 0.24 micromolar Taqman probe, 0.2 microgram/microliter BSA, 0.2% Tween 20, and 1 microliter of purified bacteria RNA. To be able to distinguish every reaction, a combination of two fluorescence dyes, Texas red and Alexa 680, was added at different concentrations to each cocktail as its unique barcode. A 48-parallel drop maker was then used to generate drops from all PCR cocktails simultaneously in a pressure-driven chamber. See, e.g., Int. Pat. Apl. Pub. No. WO 2014/186440, published on Nov. 20, 2014, incorporated herein by reference in its entirety. The resulting drops were collected in a PCR tube and covered with mineral oil to prevent evaporation. The following RT-PCR protocol was used: 50° C. for 20 min, 95° C. for 10 min, 40 cycles of 95° C. for 30 s, 60° C. for 5 min and 72° C. 1 min.

Fluorescence detection of drops after second-round digital PCR. After amplification, the drops were re-injected into the microfluidic reading and sorting device. To achieve a stream of evenly spaced drops for detection, flows from the drops and HFE-7500 oil with 1% surfactant were combined in a "T" junction, where the flow rate of the drops was 15 microliters/h and that of the oil was 180 microliters/h. This stream flowed through a 25 micrometer×25 micrometer channel, and the drops passed the focal point of the excitation laser (488 nm). The fluorescence of each drop was collected by a microscope objective and focused onto a photomultiplier tube (PMT) from Hammamatsu. The pulses were acquired by a real-time field-programmable gate array card from National Instruments and recorded by a LabView program and analyzed using MATLAB code. From each drop, three colors were detected: green, Taqman probe signal; red, Texas red; far red, Alexa 680, where red and far red correspond to a certain gene specific primer pair. See, e.g., Table 1.

Evaluation of antimicrobial drug efficacy. To evaluate the antimicrobial drug's efficacy, the number of gene specific mRNA from the sample, with and without antibiotic treatment, was detected, and the numbers between these two samples were compared.

TABLE 1

Primers for amplifying bacteria RNA

| ECHS_A2938_QUEF | F-5'-GCCTCTGTTCGTCTCGACATC-3'<br>R-5'-ACCACGTTTTCGCCCTCTTT-3'<br>Taqman: FAM-CACCGCGCCGATACG-MGB |
|---|---|
| ECHS_A2835_RECA | F-5'-GACGCGTTTTAATAACTGGGATGAG<br>R-5-GCAGAAGCGTAACAGGTCATTAAAG<br>Taqman: FAM-CTGGAGCGCGACTTAA-MGB |
| ECHS_A0486_RIBH | F-5'-GCACTGCCCACTTTGAATATGTC<br>R-5'-GCTGTCCTGGGCAACATG<br>Taqman: FAM-CCAGGCCGTTGCTTG-MGB |

Example 4

Figure 2:
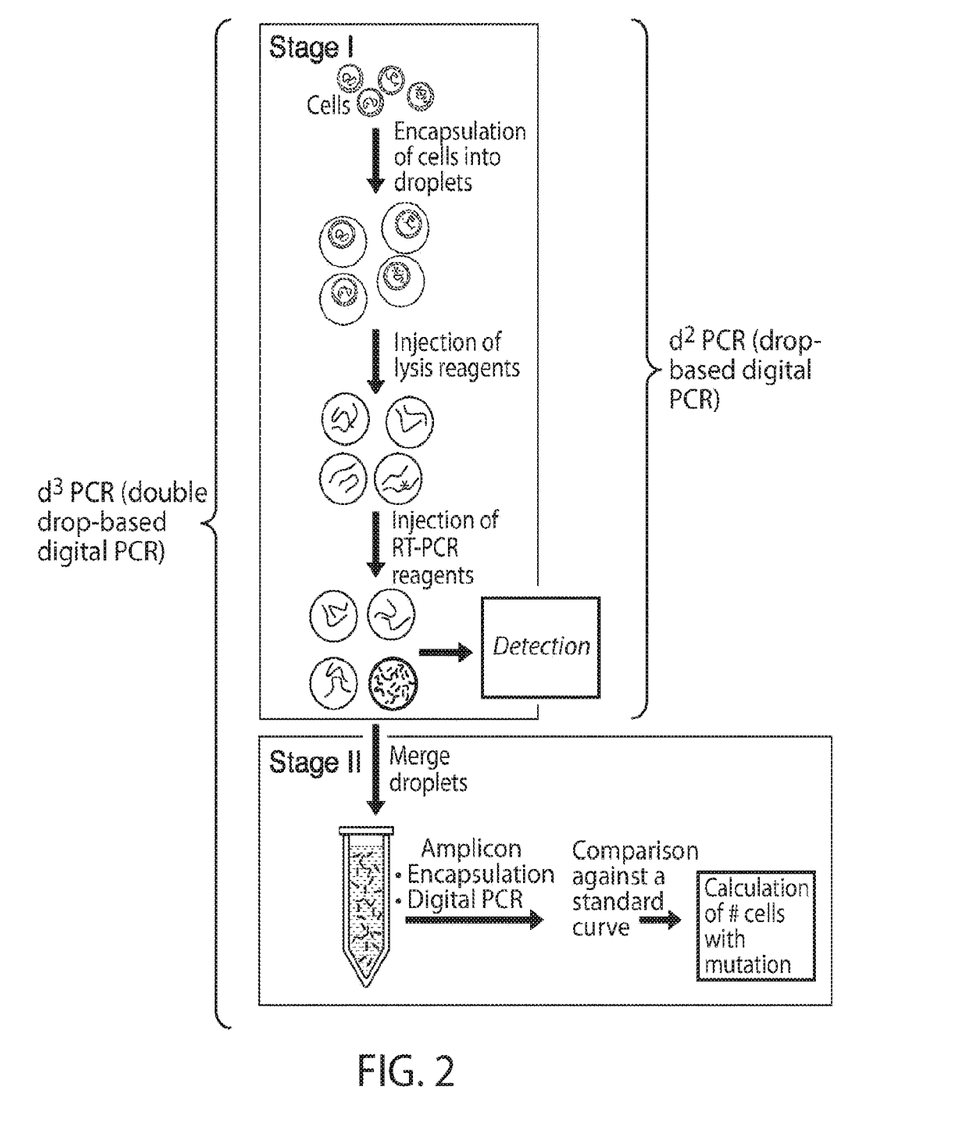
FIG. 2 illustrates a technique for PCR in accordance with certain embodiments of the invention.

For the detection of rarer populations of cells, such as one in a million cells, this example uses two rounds of drop-based digital PCR to perform detection. After the first round of drop-based digital PCR, pooled mutated amplicons are re-encapsulated using a Poisson distribution to ensure <30% of droplets contain templates, are subjected to digital PCR and the bright droplets are counted by fluorescence detection (FIG. 2).

Figure 3A:
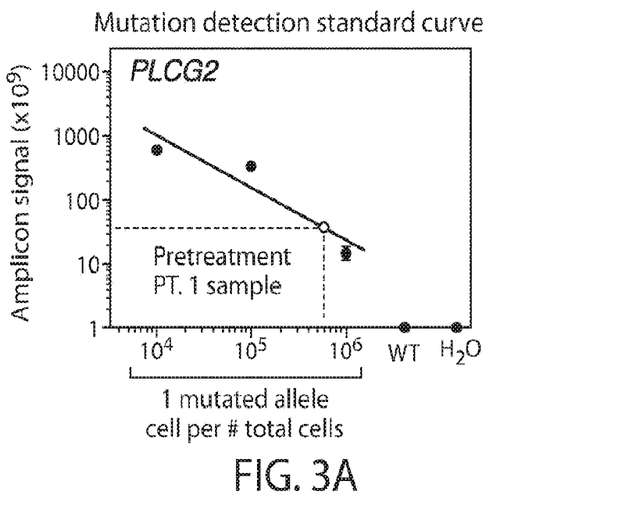
FIGS. 3A-3B illustrate data illustrate detection of mutants using an embodiment of the invention.

Using two rounds of drop-based digital PCR, a standard curve is generated from PBMC spiked with known numbers of cells from the 30019 cell line, engineered to stably express mutated PLCG2-M1141R, and reliable detection of 1 in $10^4$, $10^5$ and $10^6$ cells with the PLCG2 mutation was observed, compared to $10^6$ cells without the mutation, or the negative water control (FIG. 3A).

Figure 3B:
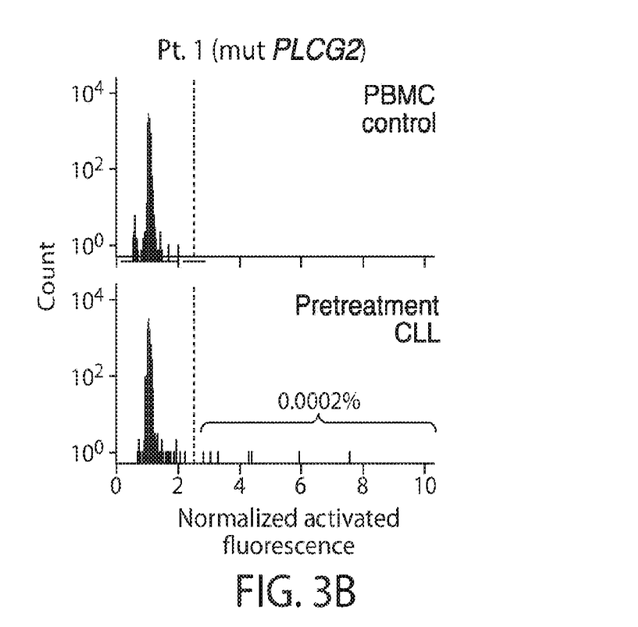

In this fashion, 1 in 500,000 pretreatment cells of Patient 1 were detected with mutated PLCG2-M1141R, of similar order of magnitude as mathematical calculations (FIG. 3B). Altogether, these results confirm that pretreatment samples carry the capacity to contain resistant subclones prior to the initiation of targeted inhibition of BTK, albeit at rare frequencies.

The data in FIG. 3A were generated as follows:

1. Cells carrying wild-type PLCG2-M1141R and mutant PLCG2-M1141R were mixed at 10,000:1, 100,000:1 and 1,000,000:1 ratio, respectively.

2. The cell mixture was encapsulated with a RT-PCR cocktail into drops and RT-PCR performed. The primers used for RT-PCR are mutation specific primers. The number of the cells encapsulated into drops is 3,000,000 in total per sample, which means there are 300, 30, and 3 cells in each sample.

3. The emulsions were broken, e.g., with a surfactant. The amplicons were collected and re-emulsified the amplicons with a PCR cocktail into drops. The primers used for PCR are also mutation specific primers. After amplification, droplets were counted.

4. From the counting result, the number of amplicons from the cells originally added were calculated.

5. A standard curve was prepared and used to show that there is a linear correlation between the number of amplicons generated (Y axis) and the number of cells that were added (X axis). This could be used to determine how many amplicons were generated from a single mutant cell.

For FIG. 3B, with a real sample and CLL pretreatment, steps 1-4 were used. This could be used to determine how many amplicons were generated in total. Finally, this total number divided by the number of amplicons one mutant cell can generate was used to determine how many mutant cells were in the sample. For example, if there are 6 mutant cells in 3,000,000 cells, the ratio of mutant to wild-type is 1:500,000, shown in FIG. 3B as a number (0.0002%) and FIG. 3A as a data point on the standard curve. In contrast, the PBMC control did not show mutant amplicons.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   encapsulating cells within a plurality of microfluidic droplets, including at least a first cell type and a second cell type, wherein the first cell type is present at a ratio of at least 1,000:1 of the first cell type relative to the second cell type;
   lysing at least some of the cells within the plurality of droplets to release nucleic acids from the cells into the interior of the droplets;
   within the interior of the droplets, applying conditions able to selectively amplify a target nucleic acid sequence suspected of being present within the nucleic acids released from the second cell type but not the first cell type;
   combining the interiors of the droplets together to form a combined fluid; and
   determining amplified nucleic acids contained within the combined fluid,
   wherein determining the amplified nucleic acids comprises determining the amplified nucleic acids using PCR.

2. The method of claim 1, wherein the cells comprise human cells.

3. The method of claim 1, wherein the cells comprise cancer cells.

4. The method of claim 1, wherein the cells comprise blood cells.

5. The method of claim 1, wherein the cells comprise bacteria.

6. The method of claim 1, wherein the target nucleic acid sequence is a DNA sequence.

7. The method of claim 1, wherein applying conditions able to selectively amplify a target nucleic acid sequence comprises applying conditions able to cause amplification via PCR.

8. The method of claim 7, wherein applying conditions able to selectively amplify a target nucleic acid sequence comprises applying conditions able to cause amplification via RT-PCR.

9. The method of claim 1, wherein applying conditions able to selectively amplify a target nucleic acid sequence comprises adding a polymerase to at least some of the interior of the droplets.

10. The method of claim 1, wherein at least some of the plurality of droplets comprises deoxyribonucleotides.

11. The method of claim 1, wherein at least some of the plurality of droplets comprises primer.

12. The method of claim 1, wherein applying conditions able to selectively amplify a target nucleic acid sequence comprises adding primer to at least some of the interior of the droplets.

13. The method of claim 1, comprising applying conditions able to selectively amplify the target nucleic acid sequence by at least $10^3$ times.

14. The method of claim 1, wherein the droplets have a distribution of diameters such that no more than about 5% of the microfluidic droplets have a diameter less than about 90% or greater than about 110% of the overall average diameter of the microfluidic droplets.

15. The method of claim 1, wherein combining the interiors of the droplets together to form a combined fluid comprises bursting the droplets to release the interiors of the droplets together.

16. The method of claim 1, wherein combining the interiors of the droplets together to form a combined fluid comprises coalescing the droplets together.

* * * * *

SEQUENCE LISTING

```
<160> NUMBER OF SEQ ID NOS: 12

<210> SEQ ID NO 1
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 1
gggtaagtgg catgagcaag aaagaacc                                          28

<210> SEQ ID NO 2
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 2
tttctgcgct ttgtggttta tgaa                                              24

<210> SEQ ID NO 3
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 3
acacaggaga aggtgacatt tgaa                                              24

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide
```

-continued

<400> SEQUENCE: 4
gcctctgttc gtctcgacat c                               21

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
accacgtttt cgccctcttt                                 20

<210> SEQ ID NO 6
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 6
caccgcgccg atacg                                      15

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
gacgcgtttt aataactggg atgag                           25

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
gcagaagcgt aacaggtcat taaag                           25

<210> SEQ ID NO 9
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 9
ctggagcgcg acttaa                                     16

<210> SEQ ID NO 10
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 10
gcactgccca ctttgaatat gtc                             23

<210> SEQ ID NO 11
<211> LENGTH: 18

```
<212> TYPE: DNA
<213> ORGANISM: Artificial Sequence
<220> FEATURE:
<223> OTHER INFORMATION: Synthetic Polynucleotide

<400> SEQUENCE: 11
gctgtcctgg gcaacatg                                                 18

<210> SEQ ID NO 12
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 12
ccaggccgtt gcttg                                                    15
```